US008280470B2

(12) United States Patent
Milner et al.

(10) Patent No.: US 8,280,470 B2
(45) Date of Patent: Oct. 2, 2012

(54) ANALYTE SENSOR METHOD AND APPARATUS

(75) Inventors: Thomas E. Milner, Austin, TX (US); Nathaniel J. Kemp, Austin, TX (US); Paul Castella, San Antonio, TX (US)

(73) Assignee: Volcano Corporation, San Diego, CA (US)

( * ) Notice: Subject to any disclaimer, the term of this patent is extended or adjusted under 35 U.S.C. 154(b) by 1275 days.

(21) Appl. No.: 11/935,265

(22) Filed: Nov. 5, 2007

(65) Prior Publication Data
US 2008/0119701 A1 May 22, 2008

Related U.S. Application Data

(60) Provisional application No. 60/864,280, filed on Nov. 3, 2006.

(51) Int. Cl.
*A61B 5/1455* (2006.01)
(52) U.S. Cl. .......................................... 600/310; 600/316
(58) Field of Classification Search .................. 600/309, 600/310, 316, 322, 342, 473, 476; 356/402, 356/450
See application file for complete search history.

(56) References Cited

U.S. PATENT DOCUMENTS

| 4,682,895 A * | 7/1987 | Costello ........................ 356/402 |
| 6,208,415 B1 | 3/2001 | De Boer et al. ............... 356/351 |
| 6,501,551 B1 | 12/2002 | Tearney et al. ............... 356/477 |
| 6,584,335 B1 * | 6/2003 | Haar et al. ..................... 600/322 |
| 6,665,456 B2 | 12/2003 | Dave et al. ....................... 385/11 |
| 6,952,603 B2 * | 10/2005 | Gerber et al. ................. 600/310 |
| 7,177,491 B2 | 2/2007 | Dave et al. ....................... 385/11 |
| 2004/0126048 A1 | 7/2004 | Dave et al. ....................... 385/11 |
| 2005/0171433 A1 | 8/2005 | Boppart et al. ............... 600/473 |
| 2006/0029634 A1 | 2/2006 | Berg et al. ..................... 424/422 |
| 2006/0098927 A1 | 5/2006 | Schmidt et al. ............... 385/129 |

OTHER PUBLICATIONS

Siwy, Z., et al., "Electro-responsive asymmetric nanopores in polyimide with stable ion-current signal", *Applied Physics A: Materials Science & Processing*, 75:5, 781-785 (Mar. 2003)—Abstract only.
PCT International Search Report, pp. 1-5 (May 2008).
Written Opinion of the International Searching Authority, pp. 1-13 (May 2008).
E. Kim, et al., "Fiber-Based Single-Channel Polarization-Sensitive Spectral Interferometry", Journal of the Optical Society of America, vol. 23, No. 6, pp. 1-11, (Jun. 2006).

* cited by examiner

*Primary Examiner* — Eric Winakur
*Assistant Examiner* — Chu Chuan (JJ) Liu
(74) *Attorney, Agent, or Firm* — Thomas C. Meyers; Brown Rudnick LLP

(57) ABSTRACT

The invention generally relates to systems, methods, and apparatuses for an analyte sensor. In one aspect, an analyte sensing device comprises a sensor body member including at least one nanopore and an optical conduit in optical communication with the sensor body member. The optical conduit transmits optical energy to the sensor body member and receives reflected optical energy back from the sensor body member. A photodetector is optically coupled to the optical conduit to determine an optical parameter from the reflected optical energy.

24 Claims, 9 Drawing Sheets

ANALYTE SENSOR METHOD AND APPARATUS

CROSS-REFERENCE TO RELATED APPLICATIONS

The present application claims the benefit of U.S. Provisional Application Ser. No. 60/864,280, filed Nov. 3, 2006. The aforementioned application is herein incorporated by reference in its entirety.

BACKGROUND OF THE INVENTION

The present invention relates generally to analyte sensors. More specifically, the invention relates to analyte sensors using Optical Coherence Tomography (OCT).

In OCT, light from a broad band light source is split by an optical fiber splitter with one fiber directing light to a sample path and the other optical fiber directing light to a reference path mirror. The distal end of the sample path can be interfaced with a scanning device, or the like. The reflected light from the scanning device is recombined with the signal from the reference mirror forming interference fringes (measured by a photovoltaic detector) allowing precise depth-resolved imaging or optical measurements to be taken. OCT has the potential to measure the concentrations of numerous analytes.

While there are numerous procedures to measure analytes non-invasively, there is a need in the art to measure analytes internally. Specific problems arise when optically measuring analytes internally within a vessel, such as backscattering of light due to particulates, cells, and the like. The present invention solves these problems, as well as others.

SUMMARY OF THE INVENTION

Provided herein are systems, methods and compositions for an analyte sensor.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE FIGURES

The accompanying drawings, which are incorporated in and constitute a part of this specification, illustrate aspects of the methods, apparatuses, and systems and together with the description, serve to explain the principles of the methods, apparatuses, and systems.

DETAILED DESCRIPTION OF THE PREFERRED EMBODIMENTS

The methods, apparatuses, and systems can be understood more readily by reference to the following detailed description of the methods, apparatuses, and systems and the Examples included therein and to the Figures and their previous and following description.

Figure 1:
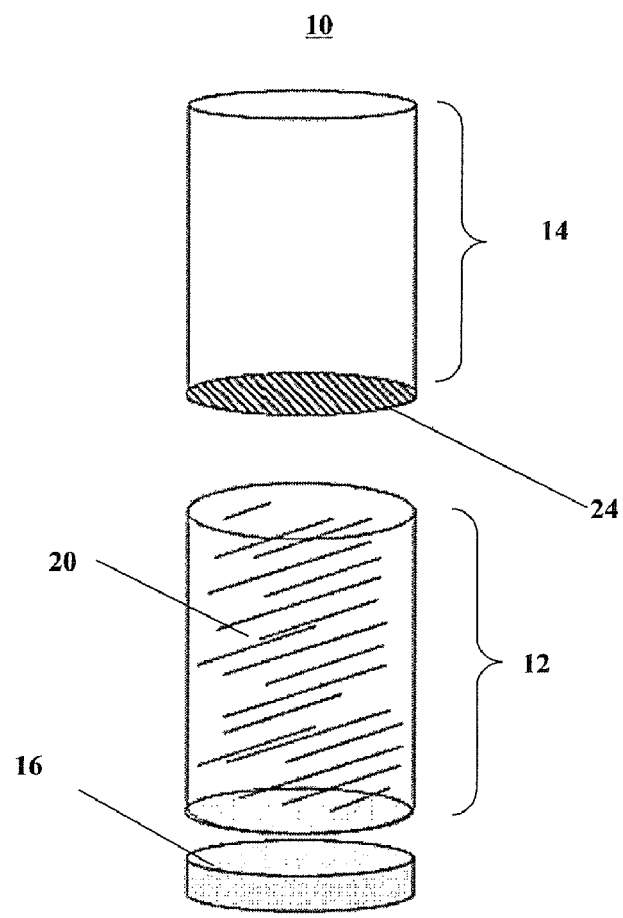
FIG. 1 is a perspective view of the analyte sensor 10.
Figure 2A:
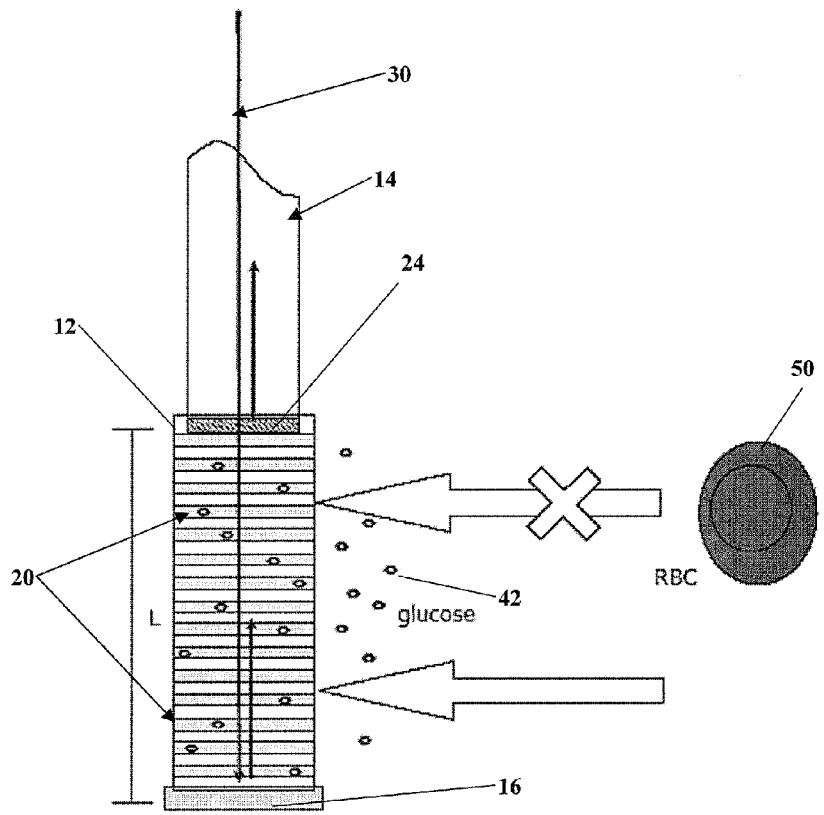
FIG. 2 is a diagram of the sensor body element 12.
Figure 2B:
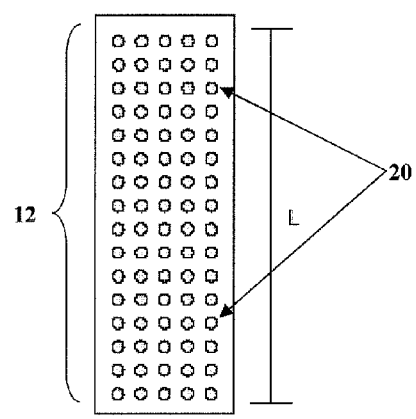

Generally speaking, the analyte sensor 10 comprises a sensor body element 12, an optical conduit 14, and a mirror surface 16, as shown in FIG. 1. The sensor body element 12 includes at least one nanopore 20, where the nanopore 20 is optically coupled to the optical conduit 14. The conduit 14 includes a semi-mirrored surface 24 on the distal end of the conduit 14, where the semi-mirrored surface 24 is coupled to the proximal end of the sensor body element 12, as shown in FIGS. 2A and 2B. Optical energy 30 is transmitted to the semi-mirrored surface 24 through the nanopores 20, and then to the distal end of the sensor body element 12, where a mirror surface 16 is located. The optical energy 30 provides for an optical measurement of an analyte 42 contained therein, which can be determined by a phase and polarization sensitive OCT system in one embodiment of the invention. In the phase and polarization sensitive OCT system, the polarization state of the optical energy 30 can be varied and coupled into the optical conduit 14, while the nanopores 20 provide a multiplicity of backreflections from the optical energy 30. The multiplicity of light reflections returning from the nanopores 20 to the optical conduit 14 recombine with the light reflecting from a reference surface to form interference fringes (measured by a photovoltaic detector) allowing phase and polarization sensitive detection of light reflecting from the nanopores 20. Analysis of the optical pathlength of the light reflected from the nanopores 20 and the variation of the polarization state of light reflected from the nanopores 20 identifies and determines the analyte concentration in the nanopores 20. It is to be understood that a variety of optical parameters or spectroscopic measurements can be collected from the sensor body element 12. The OCT systems are only examples of phase sensitive spectral domain OCT systems and are not intended to suggest any limitation as to the scope of use or functionality of OCT architectures. Neither should the OCT systems be interpreted as having any dependency nor requirements relating to any one or combination of components illustrated in the exemplary OCT systems.

Accordingly, "analyte" is any substance or chemical undergoing analysis of concentration, identification or investigation. More particularly, the analyte 42 can include carbohydrates, lipids, and proteins. In one embodiment, the analyte 42 is glucose. Alternatively, the analyte 42 can be located within a patient. In order to measure the analyte 42 located within the patient, the analyte sensor 10 is operably coupled to a catheter (not shown). The catheter is provided to obtain optical measurements of analytes within vessels of a patient. Catheters are generally known in the medical arts, i.e. any tube that can be inserted into a body cavity duct or balloon catheters, over-the-wire catheters, and the like. Optionally, the sensor body element 12 is coupled to any kind of probe (not shown) for internally measuring the analyte concentration within a body lumen. The probe can be an endoscopic probe for measuring the analyte concentration within the body lumen, such as a fiber optic probe and the like. Alternatively, the probe can be used for external measurements of an analyte, i.e. after a patient's blood has been extracted. Such measurement of analyte concentration has wide applications in a variety of clinical operations, as readily apparent to those skilled in the medical arts.

Figure 11:
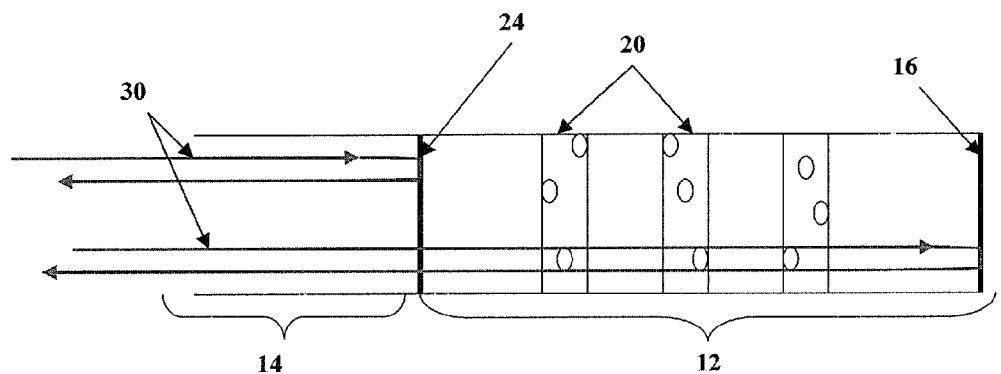
FIG. 11 is one embodiment of the sensor body element 12.

The sensor body element 12 is optically coupled and in optical communication with the optical conduit 14, as shown in FIG. 2A. The optical conduit includes a semi-mirrored surface 24 to provide backreflections from the proximal end of the sensor body element 12. The distal portion of the sensor body element 12 includes a mirror surface 16 to provide backreflections from the distal portion of the sensor body element 12. The sensor body element 12 includes a length L, as shown in FIG. 2B, and can be manufactured out of glass or any other material that is transparent to optical energy, thus allowing for transmittal and reflectance of optical energy. The sensor body element 12 can be attached by optical glue, or any other adhesive, bonding, welding to permit optical energy to be transmitting efficiently and unimpeded into the sensor body element 12. In one embodiment, the sensor body element 12 preferably is 0.01-5.00 mm thick with the nanopores 20 maintaining 50% of the volume of the sensor body element 12. In one embodiment of the invention, the sensor body element 12 may be a ferrule, to allow light energy to pass through the nanopores 20 and reflect off the mirror surface 16, and the semi-mirrored surface 24 as shown in FIG. 11. Alternatively, the sensor body element 12 may be an optical waveguide, modified with the semi-mirrored surface 24 and the nanopores 20. In one embodiment of the invention, the sensor body is made of glass and is attached to the optical conduit 14 by epoxy or optical glue.

Figure 3:
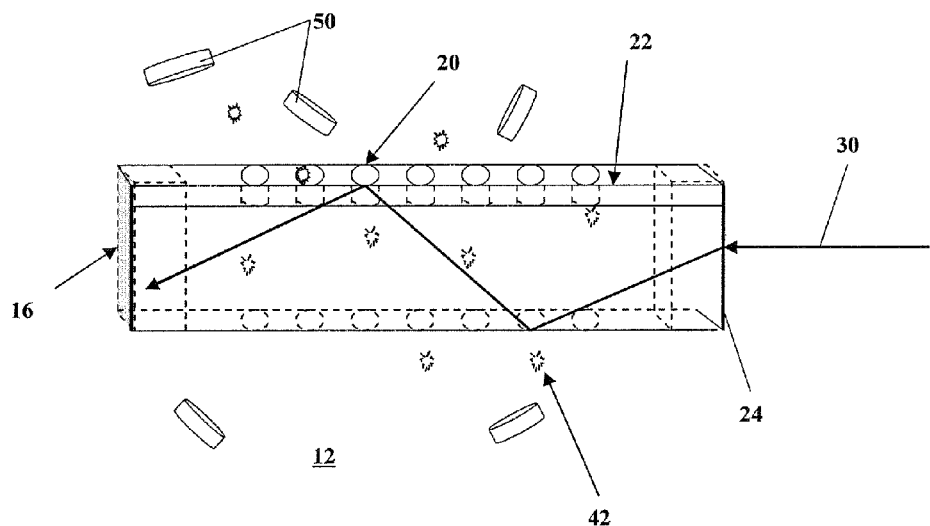
FIG. 3 is representational diagram of the diffusion of the analyte into the nanopore 20.
Figure 4:
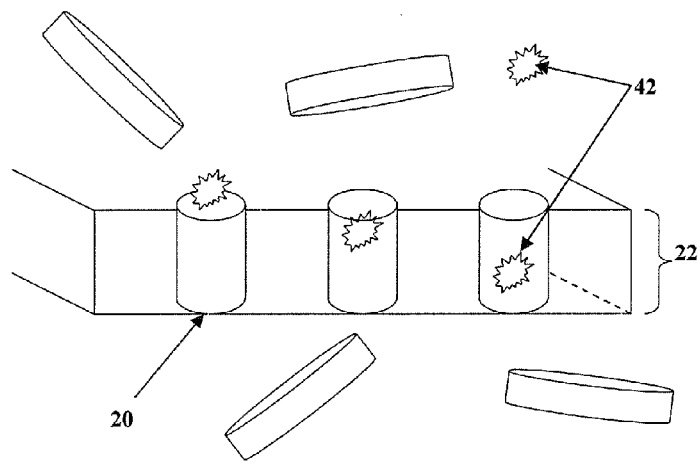
FIG. 4 is a diagram of the nanopores 20 within the coating 22

In another embodiment, the sensor body element 12 can be coated with a nanoporous coating 22, as shown in FIG. 3. The nanoporous coating 22 may be deposited to form a thin film of 100 nm thick. The nanoporous coating permits the diffusion of the analyte into the sensor body element while excluding red blood cells 50, whereupon optical energy 30 interacts with the semi-mirror surface 24 and the mirror surface 16. FIG. 4 shows an expanded view of the nanoporous coating 22, whereby the analyte diffuses into the nanopores 20 and the red blood cells 50 are prevented from entering the sensor body element 12. Alternatively, the sensor body element 12 may include a surfactant coating as to allow the refractive index of the glass material to be maintained, while permitting and/or assisting diffusion of the analyte 42 into the nanopore 20, as shown in FIG. 3. Alternatively, the surfactant coating can be changed in a controlled manner. While glass is typically hydrophobic, the surfactant will create hydrophilicity around the nanopore 20 to permit diffusion of the analyte into the nanopore 20, as shown in FIG. 3. Surfactants are readily known in the art, i.e. wetting agents that lower the surface tension of a liquid, allowing easier spreading, and lower the interfacial tension between two liquids. In one embodiment, the surfactant coating 22 is titanium dioxide, approximately 100 nm thick and a meso-porous thin film. The titanium dioxide layer can be birefringent, where two polarization modes will see birefringent film. Alternatively, the sensor body element 12 can coated with nanoparticles, which maintain the refractive index of the glass material and permit diffusion of analyte into the nanopore 20. Alternatively, the coating can include heparin or an anti-coagulant in combination with the surfactant material. Heparin prevents clotting by clotting factors and other blood components, as to prevent the nanopore 20 from clotting.

The nanopores 20 are to be structured to allow analyte molecules 42 to flow in and out of the nanopores 20, as shown in FIGS. 2 and 4. The size of the nanopores 20 can be specific for the particular analyte being identified and/or measured. "Nanopore" is any pore on the order of $1 \times 10^{-9}$ m to $300 \times 10^{-9}$ m. Alternatively, the size of the nanopores 20 can be set at about 10 nanometers, so that water and glucose 42 can diffuse through the pores while excluding red blood cells 50. Alternatively, the pore size can be optimized to permit form-birefringence in the sensor body element 12. The surfactant coating 22 layer is birefringent, where one polarization mode will not see birefringence, but 2 polarization modes will see birefringence film layer. In one embodiment, the nanopores 20 are oriented perpendicular to a light direction and contain the analyte therein, as shown in FIG. 2. The optical pathlength of light propagating through the sensor body element 12 is dependent on the analyte concentration in the pore. In order to measure optical pathlength of light propagating through the sensor body element 12, the phase sensitive OCT system is used to estimate the analyte concentration in the nanopores 20. The magnitude of form-birefringence of the sensor body element 12 is dependent on the analyte concentration in the pore, the refractive index of surrounding material, and the fractional volume of the pores. The polarization sensitive OCT system measures form birefringence in the sensor body element 12. The measured form birefringence of the sensor body element 12 typically includes a nanopore 20 with a diameter less than 200 nm.

In one embodiment, the nanopores 20 are cylindrical in form, as shown in FIG. 2. However, the nanopores 20 can be any shape desirable to obtain an optical measurement. In one embodiment, the nanopores 20 can be in chemical equilibrium with the blood plasma by the operation of slots (not shown). Alternatively, the nanopores 20 can be designed to be specific for glucose diffusion. In one embodiment, the nanopores 20 are perpendicular to the direction of light propagation in the sensor body element 12 for form-birefringence measurements, as shown in FIG. 2. In another embodiment, all the nanopores 20 are parallel and oriented in the same direction for the form-birefringence measurement. Alternatively, if the nanopores 20 are constructed in a mesoporous thin film 22, as in FIG. 3, the nanopores 20 are constructed within the thin film 22 to permit the diffusion of the analyte 42. In such an embodiment, the nanopores 20 can either be symmetrical or asymmetrical.

Fabrication of Nanopores

Fabrication of the nanopores can take place by several methodologies. A porous glass may be attached to the end of the optical fiber, which includes the nanopores. Alternatively, the optical fiber itself may include the nanopores, where the cladding includes the nanopores and coats the core of the optical fiber. In this case, the optical fiber is made by a sol gel process to give the glass a nanoporous structure. The modified sol gel process includes optically transparent amorphous silica produced by forming interconnections in a polymeric network of organosilicon. A cladding is produced by heating such a material is a nanoporous glass matrix. The end of the cladding and the beginning of the cladding can be modified to include the mirrored surfaces. The cladding is formed by the sol gel solution of oligomeric silica with no dopants, which is dip coated and then heated to form the nanopore structure.

Alternatively, the nanopores 20 can be constructed by micromachining, or Focused Ton Beam ("FIB") drilling of the sensor body element. FIB is a scanning electron microscope using a focused beam of gallium ions as a gallium liquid metal ion source (LMIS). In a Gallium LMIS, gallium metal is placed in contact with a tungsten needle and heated. Gallium wets the tungsten, and a huge electric field (greater than $10^8$ volts per centimeter) causes ionization and field emission of the gallium atoms. These ions are then accelerated to an energy of 5-50 keV (kiloelectronvolts), and then focused onto the sample by electrostatic lenses. A coating of gold or other metal will help reduce the charge produced by the Gallium ions. Typical 4" silicon wafers are 400-600 µm thick may be used, alternatively silicon nitride membranes may be drilled by FIB. The nanopores can be FIB drilled anywhere between 10-500 nm in diameter.

Alternatively, the nanopores 20 can be constructed by a nanoimprinter on a ferrule or an optical fiber. A nanoimprinter which fabricates nanometer scale patterns and creates patterns by mechanical deformation of imprint resist and subsequent processes (Nanonex, N.J.). The imprint resist is typically a monomer or polymer formulation that is cured by heat or UV light during the imprinting. Adhesion between the resist and the template is controlled to allow proper release. Thermoplastic nanoimprint lithography, photo-nanoimprint lithography, nanoscale contact printing, Step-and-Flash nanoimprinting, electrochemical nanoimprinting, and combined nanoimprint and photolithography can be used. The NXB200 conduct all forms of nanoimprinting, including thermoplastic, UV-curable, thermal curable and direct nanoimprinting (embossing). The NXB200 is high throughput large-area patterning of 3D nanostructures with sub-10 nm resolution and accurate overlay alignment for larger membranes than 1 $mm^2$. 10 nm diameter nanopores 20 holes are imprinted on a resist material for subsequent lift-off process. Such a process is adapted to nanoimprint nanopores on the sensor body element 12. For example, a nanoimprint stamp consisting of regular arrays of $Si_3N_4$ pyramids may prepare the nanopores. Alternatively, a polymer template, which has an array of nanometer diameter pillar patterns, is fabricated by hot embossing method using anodic aluminum oxide (AAO) template as an embossing stamp. After depositing the thin layer of silicon oxide and coating of anti-adhesion monolayer of organic film on silicon oxide, UV nanoimprint lithography was carried out with the polymer template. As a result, nano-pore array pattern, identical to anodic aluminum oxide pattern, is fabricated on silicon substrate. Residual layer of imprinted nano-pore array pattern is removed by oxygen plasma etch and thin film of Au/Ti was deposited. After lift-off process, Au/Ti dot array was also fabricated on silicon substrate.

Alternatively, the sensor body element may be manufactured by Surface-Plasmon Assisted Nanolithography, which uses near-filed interference patterns generated by surface plasmons ("SP's") to fabricate nanopores in a typical photolithography setup. Aluminum may be used as a mask material to support surface plasmons at ultraviolet frequencies. The aperture width may be around 150 nm and the periodicity may be around 300 nm. The interference pattern results from phase modulation by the mask pattern though the SP's. To transfer the optical interference pattern to the polymer structure, a negative tone chemically amplified photoresist may be used (SU-8, MicroChem, Newton, Mass.). The aluminum layer is deposited on a quartz substrate by electron beam evaporation. Focus Ion Beam drilling patterns the Al layer and the aluminum mask patterns include 1D grating nanopore pattern. After FIB patterning, the photoresist is spin coated onto the Al mask to a thickness of approximately 3 µm. A thin layer of coating release (OmniCoat, MicroChem) is applied between the resist and the mask. The photoresist is exposed to UV light for approximately 3 min through the mask using a UV aligner. The samples are then developed in a developer for approximately 1 hour and then air dried. Optionally, the post-exposure bake may be omitted.

Alternatively, the nanopores can be generated by holographic lithography, direct laser writing, phase shift mask techniques, or femtosecond laser ablation of borosilicate glass. Holographic lithography uses optical interference patterns combined with photolithography to produce periodic nanostructures by maintaining phase differences among four beams by optial path differences. Direct laser writing uses a photoresist illuminated by laser light at a frequency below the single-photon polymerization threshold of the resist. When this laser light is tightly focused inside the photoresist, the light intensity inside a small volume (the focus) may exceed the threshold for initiating multiphoton polymerization. The size and shape of these so-called voxels depend on the iso-intensity surfaces of the microscope objective, and the exposure threshold for multiphoton processes of the photosensitive medium. Lateral voxel sizes down to 120 nm for illumination at a wavelength of 780 nm are achievable for the nanopores. Phase shift mask are photomasks that take advantage of the interference generated by phase differences to improve image resolution in photolithography, either as alternating and attenuated phase shift masks. Femtosecond laser ablation can microstruture waveguides with nanopores. A femtosecond mode-locked seed beam of 14.5 nm bandwidth, pulse energies in the nanojoule range and repetition rate of 80 MHz is emitted from a Ti:sapphire oscillator pumped by a diode laser. A pulsed Nd:YLF operating at repetition rate of 1 kHz pumps the seed beam through a regenerative amplifier. Using the chirped pulse amplification technique, ultra-short pulses are generated with a FWHM pulse width of about 83 fs, 800 nm wavelength and 1 mJ maximum pulse energy.

If the sensor body element is a ferrule, the steps for assembly for the ferrule comprise (1) a ferrule having internal diameter same as OD of fiber cladding (for SMF-28: 125 um) (2) strip buffer and cleave (and polish if necessary) a segment of single-mode fiber optic cable with optical pathlength chosen based on desired interference fringe frequency (for current OCT sources, about 4 mm-6 mm); (3) coat cleaved ends of fiber segment with metal or dielectric to achieve appropriate reflectivity; (4) insert segment into ferrule (mechanical splice w/optical epoxy) followed by cleaved end of input (and output fibers); and (5) generate nanopores by micromachining or direct laser writing and the like.

Optimum reflectivity at each surface of the ferrule will be chosen to maximize interference fringe visibility (matched intensity reflected from each interface into detection path). Reflectivity can be controlled by coating the intermediate fiber segment with a carefully-deposited metal or dielectric surface on each end during assembly. For example, to calculate the optimum reflectivity (R1) of the first interface in transmission mode, we solve the following quadratic equation so that the two interfering beams have the same intensity (and max visibility): $R1=(1-R1)^2$, where solving: R1=38.1%. Quadruple and higher-order reflections will produce harmonics (with much reduced intensity) in the fringe signal; these can be removed electronically with a low-pass filter.

For the ferrule, light from swept laser source enters through the sensor body element. Some light is partially reflected at the first mirrored surface with the intermediate fiber segment, (possibly needing optical isolator to protect source), as shown in FIG. 11. The remaining light is transmitted through intermediate fiber segment and partially reflected at the nanopore 20. Optionally, the light may be also partially reflected at the end of the sensor body element. The reflected portion from the nanopore is transmitted back to first interface where it is again partially reflected. Transmitted light is discarded as previously and reflected portion makes a second forward propagation through intermediate fiber segment and is partially transmitted at second interface into an output or collection fiber. This portion interferes with the portion transmitted into the output fiber from the second interface on the initial reflection. Thus the path length delay between the two transmitted portions is twice the optical path length of the intermediate fiber segment. Detection of the interference fringes is accomplished after collection of the light with the output fiber.

Alternatively, the nanopores can be constructed with deposition technologies. Chemical vapor deposition ("CVD"), which entails the use of vaporized raw materials that combine with oxygen and solidify into glass. The principle CVD methods can be grouped into two categories. The first is those methods that utilize thermal energy to create the precursor vapor, and includes modified chemical vapor deposition ("MCVD"), outside vapor deposition ("OVD"), and vapor axial deposition ("VAD"). The second utilizes electromagnetic radiation to ionize precursor gas, thus forming a plasma from which the glass is deposited. Methods in this category include plasma CVD ("PCVD") and plasma enhanced CVD ("PECVD"). Chemical etching can remove portions of the deposited silica to form the nanopores, i.e. anisotropic wet etching by potassium hydroxide (KOH) or tetramethylammonium hydroxide (TMAH) and the like.

Figure 5:
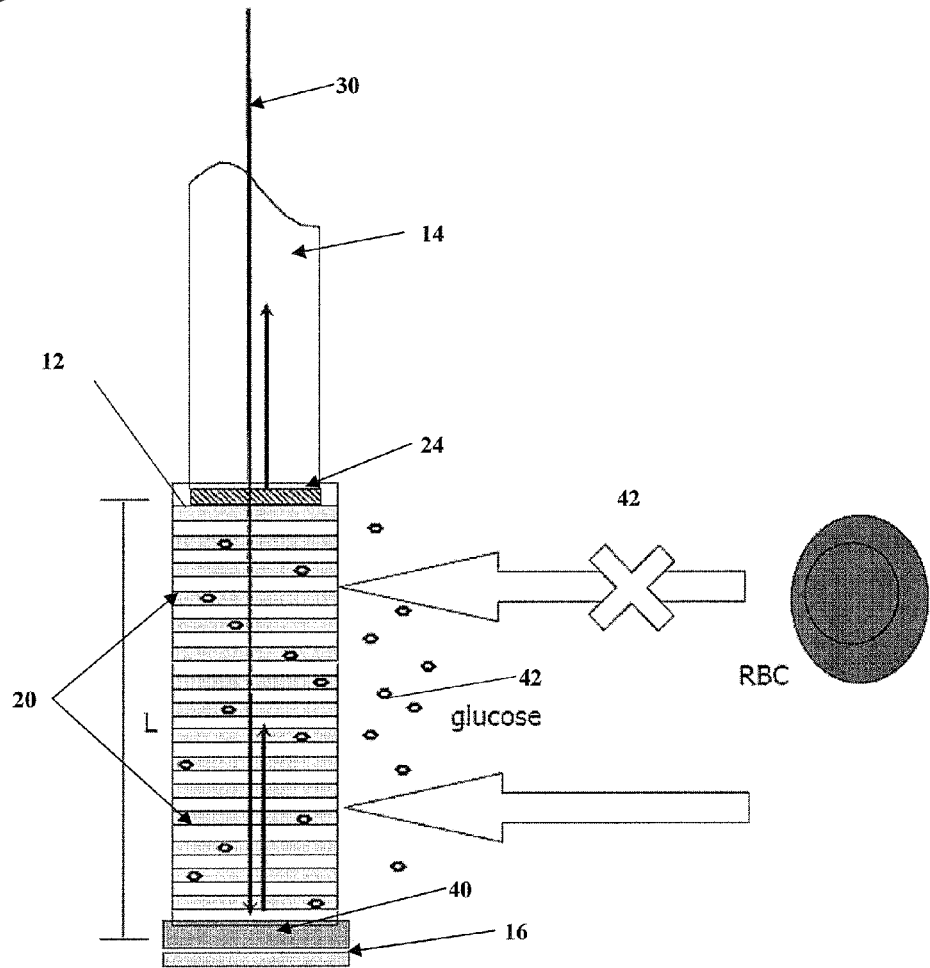
FIG. 5 is a diagram of the sensor body element 10 coupled with an OCT system and diffusion of the analyte.
Figure 6:
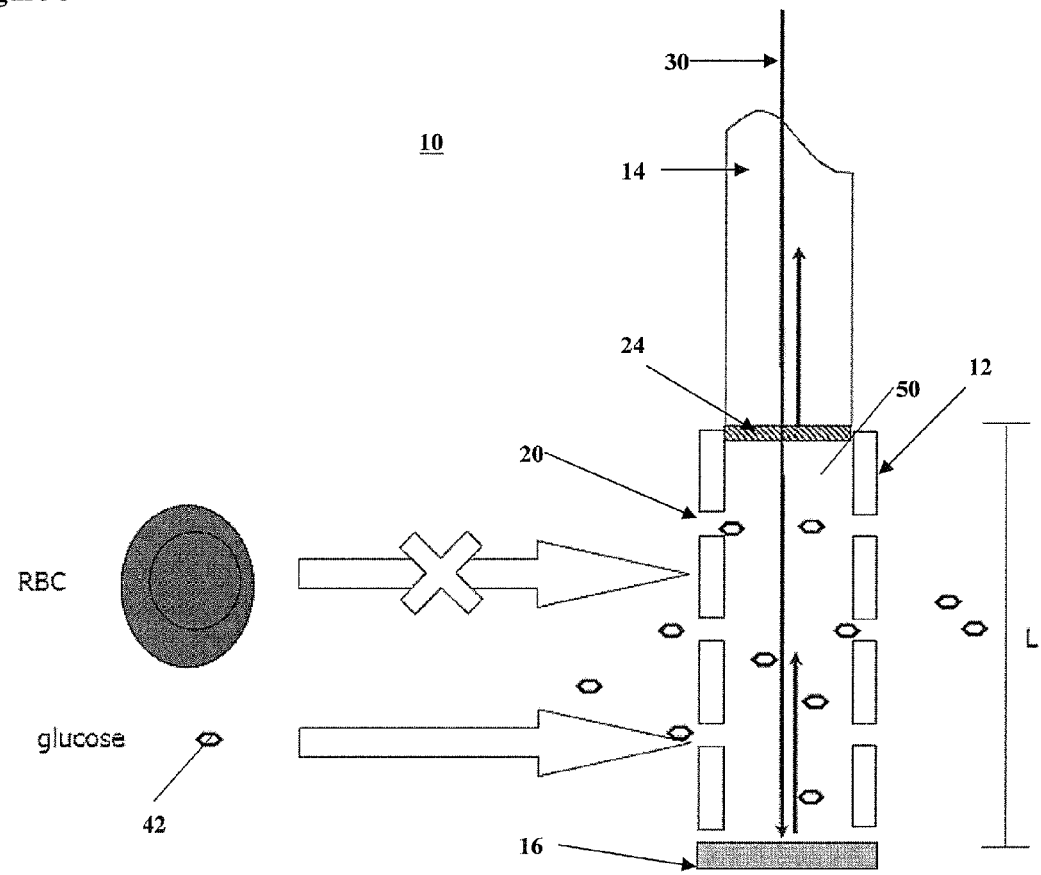
FIG. 6 is a diagram of an alternative embodiment of the sensor body element 10 coupled with an OCT system and diffusion of an analyte.

In operation, the analyte sensor 10 is connected to a single mode fiber of a sample arm in the phase and polarization sensitive OCT system. Optical energy from the phase and polarization sensitive OCT system is delivered to the optical conduit 30. A standard analysis of interference fringes formed between light reflecting from the reference surface and sensor body element 12 is completed to determine the optical path length and depth resolved polarization state of light reflecting from the sensor. Different optical parameters can be obtained by the analysis of light using phase and polarization sensitive OCT. In one embodiment of the invention, the phase sensitive OCT system measures the change in the optical pathlength, when the nanopore 20 volume is set to a known value, as shown in FIGS. 5 and 6. The nanopore 20 volume can be used to measure the refractive index of the solution inside the nanopores 20. Refractive index of the solution inside the nanopore can be related to analyte concentration in the nanopore. When the analyte concentration is measured due to optical pathlength changes in the sensor body element 12, the phase sensitive OCT system is coupled to an optical clock (not shown). Optical clocks are generally known to one skilled in the optical arts in telecommunications and high-precision optical metrology, or as understood by commonly assigned Provisional Application Ser. No. 60/949,467, entitled "Apparatus and Methods for Uniform Frequency Sample Clocking", herein incorporated by reference. Alternatively, the sensor body element 12 can be a nano-porous surface with an internal cylindrical lumen 50, as shown in FIG. 6.

In another embodiment, the sensor body element 12 is filled with a particular analyte, and then the analyte's optical parameters are monitored in a time-frame in order to deduce the concentration in the body lumen from the time variation of the analyte filling the sensor body element 12.

Figure 7A:
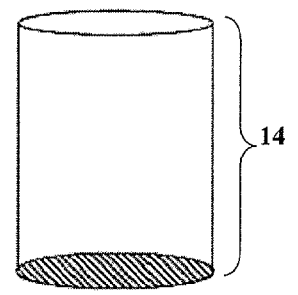
FIGS. 7A and 7B are perspective views of alternative embodiments of the sensor body element 10.
Figure 7A:
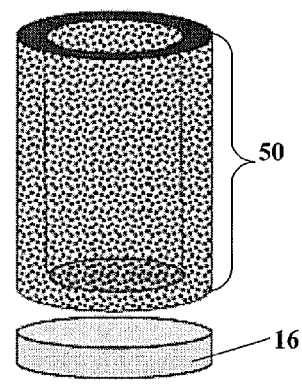
Figure 7B:
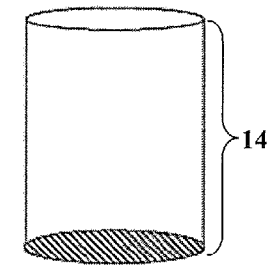
Figure 7B:
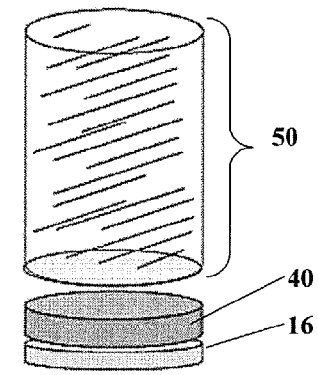

In another embodiment of the invention, the polarization sensitive OCT system measures the form-birefringence in the sensor body element 12. The form-birefringence can be related to the refractive index of the analyte solution in the nanopore 20, which is related to the analyte concentration. In this approach, the birefringence of the sensor body element 12 will vary with the refractive index of the analyte in the nanopore 20, so then depth resolved phase retardation can be measured. The birefringence of the nanopore 20 can be used to obtain another measurement of the average refractive index of the solution inside the nanopore 20. When the analyte concentration is estimated due to changes in form-birefringence in the sensor body element 12, the nanopores 20 must be asymmetrical, as in FIG. 7A. The cancelling effect of circular birefringence may be avoided by cascading the sensor body element 12 between a faraday rotator 40, as shown in FIGS. 5 and 7B. Faraday rotators 40 are generally known in the optical arts, i.e. an optical device that rotates the polarization of light due to the Faraday Effect. The faraday rotator 40 are non-reciprocal and would break the symmetry that normally would cancel the unwinding effect of the light reflecting from a surface and nulling circular birefringence of an analyte. So when circular birefringence is used to estimate the concentration of the analytes, the sensor body element 12 includes at least one Faraday rotation element 40 on the distal portion of the sensor body element 12 coupled with a polarization sensitive OCT system. Alternatively, circular and form-birefringence can be used to estimate the analyte concentration if the nanopores 20 are asymmetric and the sensing body element 12 are coupled with at least one Faraday rotation element 40 with the phase and polarization sensitive OCT system. Asymmetric nanopores 20 can be seen in FIG. 7A. For circular and form-birefringence, the trajectory of the Stokes vector on the Poincare sphere is analyzed to estimate the analyte concentration from the trajectory accounting for both circular and form-birefringence.

In another embodiment of the invention, biattenuance (sometimes called diattenuation) can also be measured to provide an additional optical measurement parameter. The dispersion of the birefringence may be sensitive to analyte concentration and serve as a secondary measurement to refine an estimate of analyte concentration. Alternatively, the change in the diffraction pattern could be measured when the nanopores 20 are arranged in parallel with a solution of the analyte 42, as shown in FIG. 2. The diffraction pattern would be changed based on the index of the analyte 42. The diffraction of the light in the sensing body element 12 will affect the magnitude of backscattered light from the sensing body element 12. Alternatively, the diffraction phenomenon can be connected to the analyte 42 that is measured.

The phase and polarization sensitive OCT system and operation can be readily understood by commonly assigned application Ser. No. 10/679,952 entitled, "Fiber-Based Optical Low Coherence Tomography" and U.S. Pat. No. 6,665,456 entitled "Method and Apparatus for Differential Phase Optical Coherence Tomography", as well as in the Provisional Application Ser. No. 60/932,546, entitled "Fiber-Based Single-Channel Polarization Sensitive Spectral Interferometry", incorporated by reference herein. More particularly, Phase Resolved Polarization Sensitive Optical Coherence Tomography (PS-OCT) is used to measure change in optical path length and form birefringence that can be used to estimate analyte concentration. The PS-OCT system measures form birefringence by calculating the phase retardation between orthogonal components of polarized light, resolved along the fast and slow axes of the sensing body element 12. The PS-OCT system measures the differential optical pathlength between light oscillating parallel and perpendicular to the cylindrical nanopores 20. The differential optical pathlength of orthogonal oscillations is different due to the nanopores 20 and dependent on the analyte concentration in the sensor. The PS-OCT system detects the phase retardation between the orthogonal light oscillations in the sensing body element 12. When the analyte exhibits circular birefringence, the sensing body element 12 includes at least one Faraday rotator element 16 to break the symmetry due to reflection of light in the sensing body element 12, as shown in FIG. 5. To estimate concentration of the analytes that exhibit circular birefringence, trajectory of the Stokes vector on the Poincare sphere corresponding to light backscattered from the sensing body element 12 is analyzed for movements orthogonal to displacements due to linear birefringence. The composite trajectory on the Poincare sphere, which includes movements due to linear form birefringence and circular birefringence of the analyte, is analyzed to estimate analyte concentration.

The analyte sensor apparatus also provides for a method to measure an analyte concentration. The method includes inserting an analyte sensor into a patient where the analyte sensor includes a sensor body element with at least one nanopore, coupling the nanopore with an optical conduit, permitting the active or passive diffusion of an analyte into the nanopore, transmitting optical energy to the sensor body element; and measuring at least one optical parameter with a detector. In one embodiment of the invention, allowing active or passive diffusion of analyte into the sensor and monitor analyte concentration with time measures the concentration of the analyte by analyzing the time-evolution of analyte concentration to more accurately estimate analyte concentration in the body lumen. After the time-evolution measurement is completed, the sensor body element is flushed and the measurement is repeated. Such flushing techniques may be operable by catheter flushes with saline.

Alternatively, the method to measure an analyte further includes generating light energy; transmitting at least a first portion of the generated light energy onto a reference reflector wherein at least a portion of the transmitted first portion of light energy is reflected by the reference reflector; transmitting at least a second portion of the generated light energy into the sensor body, wherein at least a portion of the transmitted second portion of light energy contacts an analyte located within the nanopore and wherein at least a portion of the light energy which contacts the analyte is reflected; receiving the light energy reflected by the reference reflector and the analyte; combining the received light energy, wherein the combined light energy interferes; processing the combined light energy to measure the refractive index of the analyte within the pore.

In one embodiment of the invention, the method to measure an analyte includes measuring the change in optical pathlength to refractive index of the analyte solution inside the nanopores with a phase sensitive OCT system coupled to an optical clock. Alternatively, the method to measure an analyte includes measuring the form-birefringence to measure the average refractive index of the analyte inside the nanopores with a polarization sensitive OCT system, where the nanopores are asymmetrical. In another embodiment, the method to measure an analyte includes measuring the circular birefringence with a polarization sensitive OCT system and the sensor body element coupled to at least one Faraday rotation element. Alternatively, the method to measure an analyte includes measuring circular and form-birefringence with a phase and polarization sensitive OCT system, where the sensor body element is coupled to at least one Faraday rotation element and the nanopores are asymmetrical. Generally, the method provides a means to measure the polarization state of light backscattered from the sensor element, depict trajectory of the polarization state on the Poincare sphere or the complex polarization ratio (Z) plane and analyze the trajectory to estimate the analyte concentration in the sensor.

In another embodiment, the method to measure an analyte includes filling a sensor body element with a particular analyte; monitoring the analyte's optical parameters in a time-frame; deducing the analyte's concentration from the time variation of the analyte filling the sensor body element.

Spectral Analysis of Analyte in the Eye:

An eye includes a lens for imaging onto a retina located at the back of the eyeball. Dense relatively opaque tissue, the sclera, together with a curved transparent window, the cornea, forms a chamber inside of which is the ocular lens. This lens is held in place by the ciliary body and fibrous muscle included therewith. An iris comprising opaque diffusely reflecting tissue that includes a central opening, i.e., the pupil, lies on an anterior surface of the lens. The refractive powers of the lens and the cornea combine to focus light on the retina. A tiny region approximately at the center of the retina known as the fovea comprises densely packed photoreceptor, which provides vision for fine detail. When the eye peers at a distant object, such as for example a star, the eye rotates until an image of the distant object falls on the fovea. A straight line drawn through the center of the pupil and the fovea is known as the visual axis, sometimes referred to as the line of sight. The cornea and the lens together form a cavity called the anterior chamber. The anterior chamber is filled with a transparent liquid known as aqueous humor.

The glucose concentration in the aqueous humor closely tracks the glucose concentration in the bloodstream to within a delay of only minutes. Increases in the glucose level of the blood are mimicked by proportional rises in the glucose level in the aqueous humor. Accordingly, by monitoring the glucose concentration of the aqueous humor, changes in the glucose concentration in the blood can be sensed.

Spectral interferometry can be employed to measure the index of refraction of the aqueous humor. Other optical methods can be used that monitor optical properties that are dependant on the refractive index of this fluid in the eye. Identifying and quantifying fluctuations in the index of refraction of the aqueous humor using light is preferred as it is clean, non-invasive, and relatively precise.

Spectral Analysis of Analyte outside Body

Alternatively, the sensor body of the analyte sensor can be included in an apparatus detached from a catheter. Such is an example of a device where a sample of blood taken from a patient is placed on the sensor body and the analyte concentration is measured as indicated previously.

EXAMPLES

The following examples are put forth so as to provide those of ordinary skill in the art with a complete disclosure and description of how the articles, devices, systems, and/or methods claimed herein are made and evaluated, and are intended to be purely exemplary and are not intended to limit the scope of compositions, compositions, articles, devices, systems, and/or methods. Efforts have been made to ensure accuracy with respect to numbers (e.g., amounts, temperature, etc.), but some errors and deviations should be accounted for.

Example 1

Quantitative Determination of Glucose Concentration by Swept-Source Spectral Interferometry and Spectral Phase Analysis To quantitatively measure glucose concentration in an aqueous solution this example estimates the optical path length change of the solutions by utilizing a swept-source spectral interferometry and a unique spectral phase analysis. Concentrations of the glucose solutions are in the range of 0-50 mM.

Figure 8:
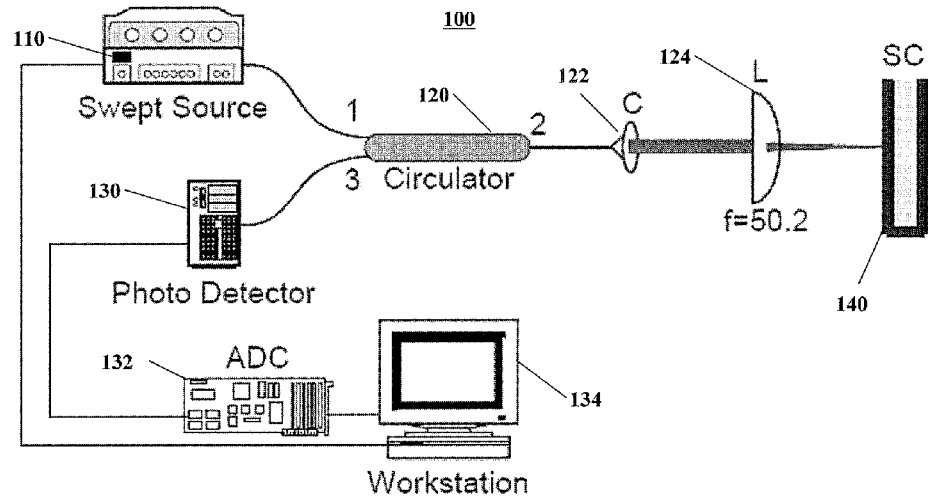
FIG. 8 is a diagram of a fiber-based common-path spectral interferometer 100.

The swept-source spectral interferometer system 100 is depicted in FIG. 8. The swept source spectral interferometer system 100 is a fiber-based common-path spectral interferometer and includes a light source 110, an interferometer, and a detector. The light source 110 is a high-resolution, broadband frequency swept laser source (Precision Photonics, TLSA1000); wavelength range 1520-1620 nm, and maximum output power 0.4 mW. The spectral line width of the swept laser is specified at 150 KHz. The interferometer is a Michelson-type common-path interferometer and includes an optical circulator 120, a collimator 122, a sample chamber 140, and a plano-convex lens 124. The optical circulator 120 includes port 1, port 2, and port 3 for input and output of light energy. The plano-convex lens 124 may include a plano-convex BK7, f=50.2 (Newport, N.J.), and the sample chamber 140 may include an Internal Diameter ("ID")=2.686 mm (NSG Precision Cells Inc). The sample chamber 140 holds the liquid sample. The detector includes a photodetector 130 (New Focus, photodetector 2011), an analog-to-digital converter 132 ("ADC") (National Instrument, AT-MIO-64E-3), and a computer workstation 134. The plano-convex lens 124 functions as a reflector for the reference and a condenser that focuses the input light into the sample chamber and also focuses the reflected and scattered light from the surfaces of the sample chamber 140 into the collimator 122. Therefore the reference path for the common-path interferometer extends from the optical circulator to the front surface of the plano-convex lens.

As shown in FIG. 8, input light generated by the swept laser source 110 is coupled into port 1 and exits through port 2 of the optical circulator 120. Light exiting port 2 is collimated and a portion of the incident light is reflected from the plano side of the lens 124 and returned to the collimator 122, which is treated as reference reflection. Transmitted light passes the lens 124 and is reflected from each surface of the sample chamber 140. Then the reflected light energy interferes with each other, and the interference fringes are coupled into the collimator and detected at the photodetector 130 after passing through the optical circulator 120 out port 3. The detected optical intensity of interfering light is converted to an electric voltage signal by the ADC 132, and is stored into the computer workstation 134. the optical frequency of the laser output is also stored in the computer workstation 134 through the universal serial bus connection from the swept source laser 110.

The recorded raw data from the swept-source spectral interferometer 100 are processed using spectral phase analysis to estimate the optical path length of the solution. In this example, data processing to determine glucose concentration includes a nonuniform Fourier transformation ("NUFT") and a multitaper spectral estimation for time-frequency analysis. For the first procedure, raw fringe data is transformed from the spectral domain to the time delay domain by a time-frequency transformation to examine depth-resolved information. Raw fringe data recorded from a commercially available frequency-swept laser uses a NUFT instead of a regular discrete Fourier transformation ("DFT") or fast Fourier transformation ("FFT") which applies only to evenly spaced data. To accommodate unequally spaced frequency data, a fast Lomb-Scargle algorithm is utilized. Lomb-scargle periodogram analysis is an approach to Fourier spectrum analysis for unevenly spaced data with less spectral leakage, and has been modified to a fast combination of Lagrange interpolation and FFT algorithm by implementing a combination of Lagrange interpolation and FFT. Alternatively, if the FFT is used, direct sampling of the evenly spaced data is achieved by clocking the swept laser source. Such clocking of the swept laser source is generally understood by commonly assigned Provisional Application Ser. No. 60/949,467, entitled "Apparatus and Methods for Uniform Frequency Sample Clocking".

Figure 9:
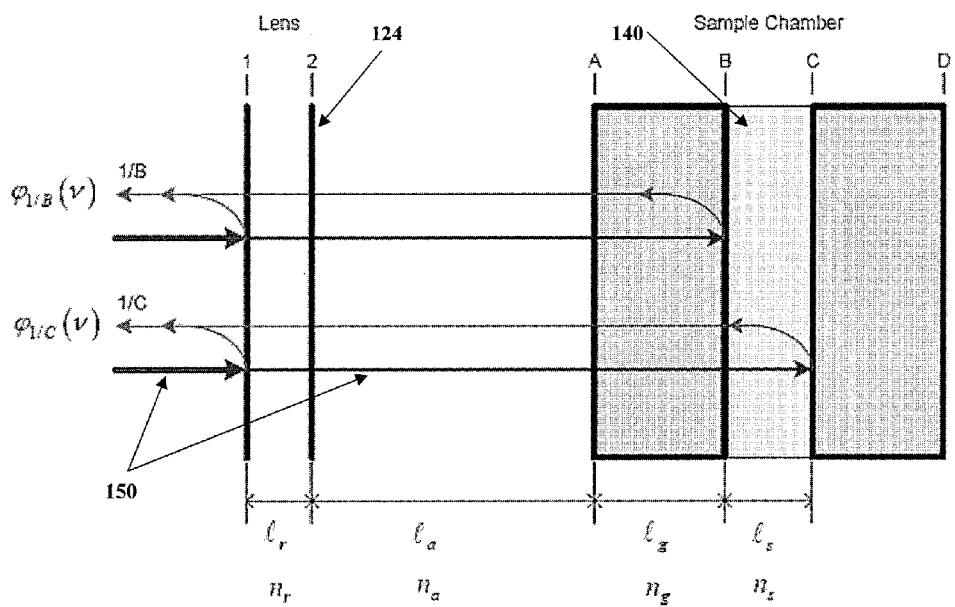
FIG. 9 is a diagram of interferometer sample path, where $\Phi_{1/C}(v)$ and $\phi_{1/B}(v)$ represent the spectral phase functions generated from 1/C and 1/B interference fringes.

Interested interference fringes isolated in the time-delay domain computed by the NUFT of the raw data are selected and arranged in order to configure the location and the size of the window that are important parameters for multitaper spectral estimation. FIG. 9 shows an illustration of the optical paths of the common-path interferometer to provide a convenient view to better understand how the common-path interferometer operates and is used to estimate location of interested interference fringes in the time delay domain. The sample chamber 140 includes two reflecting surfaces B and C, while the lens 124 includes reflecting surface 1. Single numbers and letters in FIG. 9 represent corresponding surfaces which reflect incident light and where $l_r$, $l_a$, $l_g$, and $l_s$ are physical lengths of the lens, air, glass, and sample. Optical energy 150 reflects off the lens at surface 1 and reflects of surfaces B and C. The labels 1/B and 1/C indicate the interference fringes generated by the two surfaces where the light is reflected and are of interest for data processing. FIG. 9 indicates the location of fringes in the time delay domain can be estimated by optical path length difference ("OPD") between reference and sample paths.

For the next procedure, multitaper spectral estimation is applied to the interference fringes of interest in time delay domain to transfer to the spectral domain. Multitaper spectral estimation uses a number of orthogonal tapers called Slepian sequences and/or discrete prolate spheroidal sequences and has advantages of less side-lobe contamination and stable spectral estimation. To optimize the variance and bias of the result, one can adaptively establish the weights of each taper In the last data processing procedure, spectral phase functions of interested fringes, $\phi_\alpha(\nu)$ and $\phi_\beta(\nu)$, are calculated from the results of multitaper spectral analysis of 1/C and 1/B, respectively, and they can be modeled as, $$\varphi_\alpha = \frac{2\pi}{C} \cdot \nu \cdot [\ell_r \cdot n_r(\nu) + \ell_s \cdot n_s(\nu) + \ell_g \cdot n_g(\nu) + \ell_a \cdot n_a(\nu)] \quad (1.1)$$

$$\varphi_\beta = \frac{2\pi}{C} \cdot \nu \cdot [\ell_r \cdot n_r(\nu) + \ell_g \cdot n_g(\nu) + \ell_a \cdot n_a(\nu)] \quad (1.2)$$

where $l_r$, $l_a$, $l_g$, and $l_s$ are physical lengths of the lens, air, glass, and sample; $n_r$, $n_a$, $n_g$, and $n_s$ are refractive indices of lens, air, glass, and sample, respectively. By calculating the slope of $\phi_\alpha(\nu)-\phi_\beta(\nu)$, optical path length of the sample can be extracted.

Figure 10A:
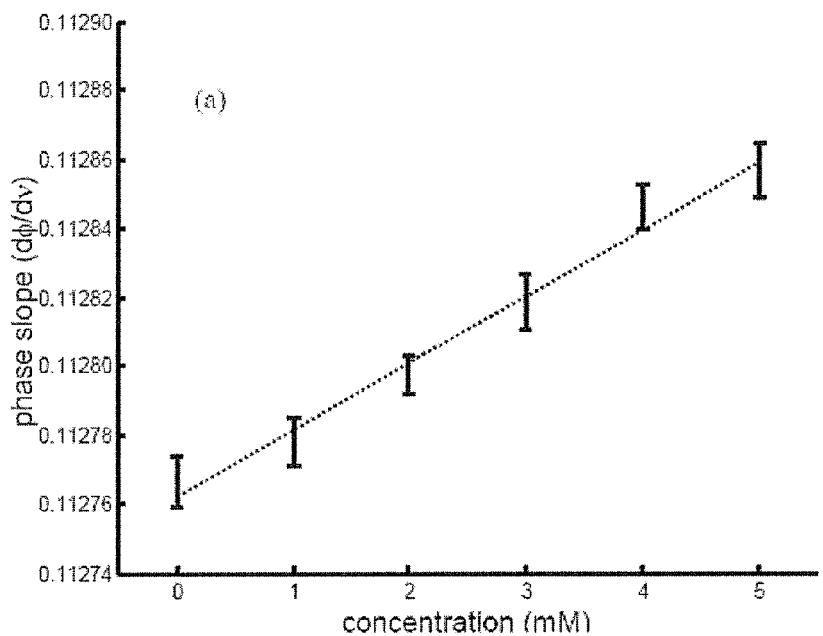
FIGS. 10A and 10B are graphs of glucose concentration measurement for 0-5 mM in 1 mM increments and 0-5 mM in 5 mM increments, respectively, where each error-bar represents the standard deviation of 20 measurements.
Figure 10B:
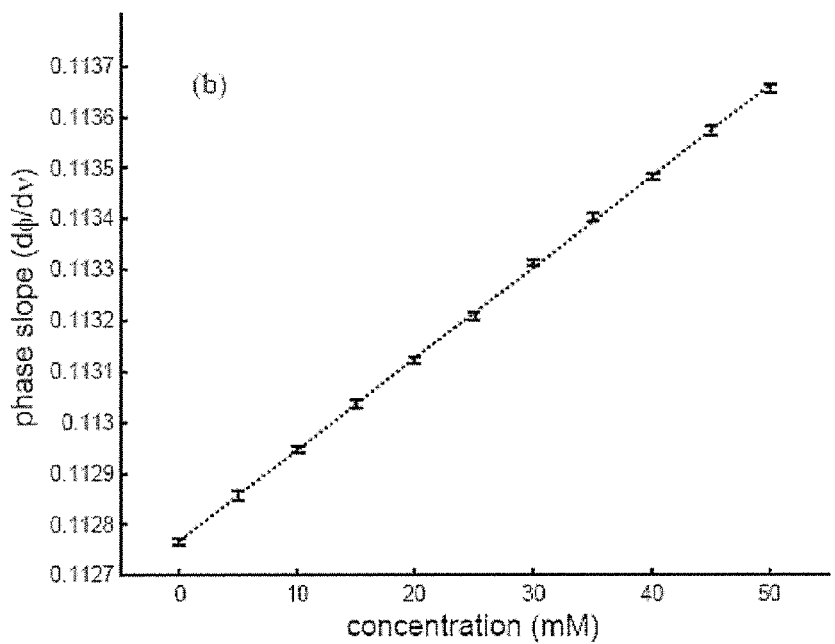

The mean frequency interval is 0.400 GHz and standard deviation (STD) is 0.0076 GHz. The fast Lomb-Scargle algorithm provides a solution of the problem caused by unevenly spaced frequency samples in the swept light source and gives advantages of faster processing speed as well as less spectral leakage. The adaptively optimized weight factor of multitaper spectral analysis for this study is $$b_k(N) = e^{\frac{(N-N_0)^2}{2\sigma^2}} \quad (1.3)$$

where $N=1, 2, 3 \ldots, 8$, $N_0=6.5$, and $\sigma=1.225$ for higher-order refractive index estimation; besides where $N=1, 2, 3 \ldots, 8$, $N_0=0.75$, and $\sigma=0.5$ for glucose measurement. FIGS. 10A and 10B shows the result of the slope of $\phi_\alpha(\nu)-\phi_\beta(\nu)$, versus various glucose concentrations in a micro-range and a macro-range, respectively. FIG. 10A shows the Glucose concentration measurement for 0-5 mM in 1 mM increments FIG. 10B shows the 0-50 mM in 5 mM increments. Each concentration has 20 experimental measurements, and error bars represent the standard deviation of 20 measurements. The dotted line is a linear regression of measure data ($\hat{Y} \times 10-5$ $X+0.11276$). Correlation coefficients and sensitivities based on root mean square error of prediction ("RMSEP") for both ranges are given as follows. Micro-range includes a Correlation coefficient of 0.993 and a Resolution of 0.86 mM. The Macro-range includes a Correlation Coefficient of 0.999 and a Resolution of 0.54 mM.

Because the B/C interference fringe indicates optical properties of the target sample and is located close to the DC noise range, it includes a significant level of noise. Therefore, 1/B and 1/C interference fringes located where DC noise does not affect are used to obtain optical path length of the target sample. The fast Lomb-Scargle algorithm accommodate unevenly spaced frequency samples and contributes to reduce calculation complexity from $O(N^2)$ to $O(N\log N)$, and multi-taper spectral analysis is well suited to minimize side-lobe contamination by use of an adaptively optimized stochastic processing.

According to FIGS. 10A and 10B, the result is highly correlated to the linear regression (correlation coefficient 0.999) and shows excellent sensitivity up to 0.54 mM. The micro-range data presents slightly lower sensitivity than that in the macro-range, but still demonstrates capability of this method to determine small changes in concentration of glucose solutions which satisfies clinical accuracy for healthy individuals.

The parameters of the lens 124 and the sample chamber 140 can be modified with the optical conduit 14 and the sensor body element 12, respectively. For example, the factors for the lens 124 are substituted for the reflective surface 24 of the optical conduit 14 and the factors for the sample chamber is substituted for the nanopores 20 and the reflective surface 16 of the sensor body element 12. Such substitutions are readily apparent to those of skilled in the art.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An analyte sensing device comprising:
   a. a sensor body member including at least one nanopore;
   b. an optical conduit in optical communication with the sensor body member, the optical conduit transmits optical energy to the sensor body member and receives reflected optical energy back from the sensor body member; and
   c. a photodetector optically coupled to the optical conduit to determine an optical parameter from the reflected optical energy,
   wherein the photodetector is optically coupled to an optical coherence tomography instrument and the optical parameter is correlated with a refractive index of the analyte.

2. The analyte sensing device of claim 1, wherein the sensor body member includes a reflective surface at the distal end of the sensor body element in optical communication with the optical conduit and the optical conduit includes a reflective surface at the distal end of the optical conduit.

3. The analyte sensing device of claim 1, wherein the optical coherence tomography instrument comprises:
   a. a light source;
   b. a polarization maintaining reference path;
   c. a polarization maintaining sample path optically aligned with the optical conduit; and
   d. a polarization maintaining detection path optically aligned with the photodetector, wherein the detection path, the source path, and the reference path are each optically connected to a path coupler.

4. The analyte sensing device of claim 1, wherein the nanopore is at least 300 nanometers.

5. The analyte sensing device of claim 3, wherein the optical coherence tomography instrument is phase sensitive to measure the change in optical path length.

6. The analyte sensing device of claim 3, wherein the optical coherence tomography instrument is polarization sensitive.

7. The analyte sensing device of claim 3, wherein the sensor body element is optically coupled with at least one faraday rotator and the optical coherence tomography instrument is polarization sensitive to measure circular birefringence.

8. The analyte sensing device of claim 3, wherein the optical coherence tomography is phase and polarization sensitive.

9. The analyte sensing device of claim 1, wherein the sensor body member is operationally coupled to a catheter.

10. The analyte sensing device of claim 1, wherein the sensor body member is substantially coated with a surfactant.

11. The analyte sensing device of claim 1 wherein the at least one nanopore are a plurality of nanopores.

12. The analyte sensing device of claim 11, wherein the nanopores are asymmetrical.

13. The analyte sensing device of claim 11, wherein an optical pathlength of the light reflected from the nanopores and a polarization state of light reflected from the nanopores determine the analyte concentration in the nanopores.

14. The analyte sensing device of claim 11, wherein the nanopores are substantially parallel to one another.

15. A method for obtaining optical measurements of an analyte comprising the steps of:
   optically coupling a sensor body element with an optical conduit, the sensor body element includes at least one nanopore and a reflective surface, and the optical conduit is operably associated with a reference reflector;
   permitting the diffusion of an analyte into the at least one nanopore;
   transmitting optical energy from the optical conduit to the sensor body element;
   reflecting optical energy from the sensor body element back to the optical conduit;
   measuring the reflected optical energy with a detector optically coupled to an optical coherence tomography instrument; and determining a refractive index of the analyte from the measured energy.

16. The method for obtaining optical measurements of an analyte of claim 15, wherein the optical conduit and reference reflector are included in the optical coherence tomography system and the method further comprises the steps of:
generating light energy from a light source;
transmitting at least a first portion of the generated light energy onto the reference reflector wherein at least a portion of the transmitted first portion of light energy is reflected by the reference reflector;
transmitting at least a second portion of the generated light energy into the sensor body, wherein at least a portion of the transmitted second portion of light energy contacts an analyte located within the at least one nanopore and wherein at least a portion of the light energy which contacts the analyte is reflected; receiving the light energy reflected by the reference reflector and the analyte;
combining the received light energy, wherein the combined light energy interferes; and processing the combined light energy to measure the refractive index of the analyte within the at least one nanopore.

17. The method for obtaining optical measurements of an analyte of claim 15 further comprises measuring the change in optical pathlength to measure the refractive index of the analyte inside the at least one nanopore where the optical coherence tomography instrument is phase sensitive and coupled to an optical clock.

18. The method for obtaining optical measurements of an analyte of claim 15, wherein the at least one nanopore are a plurality of nanopores and the method further comprises measuring a change in form-birefringence to measure an average refractive index of the analyte inside the nanopores where the optical coherence tomography instrument is polarization sensitive and the nanopores are asymmetrical.

19. The method for obtaining optical measurements of an analyte of claim 17 further comprising measuring a polarization state of the light backscattered from the sensor body element; depicting a trajectory of the polarization state on a Poincare sphere or a complex polarization ratio (Z) plane; and analyzing the trajectory to estimate the analyte concentration in the nanopore.

20. The method for obtaining optical measurements of an analyte of claim 16 further comprises: detecting a phase retardation between the orthogonal light oscillations in the sensing body element; breaking the symmetry due to reflection of light in the sensing body element with at least one Faraday rotator element; analyzing the trajectory of a Stokes vector on a Poincare sphere corresponding to the light backscattered from the sensing body element for movements orthogonal to displacements due to the linear birefringence; analyzing the composite trajectory on the Poincare sphere with movements due to linear form birefringence and circular birefringence of the analyte to estimate analyte concentration.

21. The method for obtaining optical measurements of an analyte of claim 16 further comprising estimating the concentration of the analyte with circular birefringence where the optical coherence tomography instrument is polarization sensitive and the sensor body element is coupled to at least on Faraday rotation element.

22. The method for obtaining optical measurements of an analyte of claim 16 further comprising estimating the analyte concentration with circular and form birefringence where the optical coherence tomography instrument is phase and polarization sensitive and the sensor body element is coupled to at least one Faraday rotation element.

23. The method for obtaining optical measurements of an analyte of claim 16 further comprising coupling the sensor body element with a catheter and inserting the catheter into a patient.

24. The method for obtaining optical measurements of an analyte of claim 16, further 10 comprising allowing the analyte to fill the sensor body element; monitoring the analyte by optical parameters in a time-dependent manner; and deducing the concentration of the analyte from the time variation of the analyte filling the sensor body element.

* * * * *